United States Patent [19]

Meyer et al.

[11] Patent Number: 4,944,794
[45] Date of Patent: Jul. 31, 1990

[54] N-PHENYLSULFONYL-N-TRIAZINYLUREAS

[75] Inventors: Willy Meyer, Riehen; Werner Föry, Basel; Karl Gass, Magden, all of Switzerland

[73] Assignee: Ciba-Geigy Corporation, Ardsley, N.Y.

[21] Appl. No.: 777,900

[22] Filed: Sep. 19, 1985

Related U.S. Application Data

[63] Continuation-in-part of Ser. No. 430,635, Sep. 30, 1982, Pat. No. 4,579,584.

[30] Foreign Application Priority Data

Oct. 13, 1981 [CH] Switzerland .................. 6541/81

[51] Int. Cl.$^5$ ............... A01N 43/68; A01N 43/70; C07D 251/18; C07D 251/52
[52] U.S. Cl. ............................. 71/93; 544/206; 544/208
[58] Field of Search ............... 71/93; 544/206, 208

[56] References Cited

U.S. PATENT DOCUMENTS

| | | | |
|---|---|---|---|
| 4,368,069 | 1/1983 | Chen et al. | 544/211 |
| 4,420,325 | 12/1983 | Sauers | 544/182 |
| 4,452,628 | 6/1984 | Adams | 544/211 |
| 4,492,599 | 1/1985 | Levitt et al. | 544/211 |
| 4,514,212 | 4/1985 | Meyer et al. | 544/211 |
| 4,537,619 | 8/1985 | Meyer et al. | 544/211 |

Primary Examiner—John M. Ford
Attorney, Agent, or Firm—Edward McC. Roberts; Bruce M. Collins

[57] ABSTRACT

N-phenylsulfonyl-N'-triazinylureas of the general formula

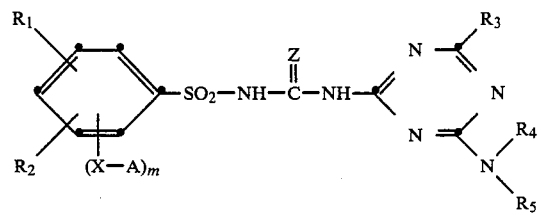

and the salts of these compounds with amines, alkali metal or alkaline-earth metal bases or with quaternary ammonium bases have good selective, pre- and post-emergence, herbicidal and growth-regulating properties.

The symbols in this formula have the following meanings;

A is a $C_1$-$C_6$-haloalkyl group,
X is oxygen, sulfur, or a sulfinyl or sulfonyl bridge,
Z is oxygen or sulfur,
m is the number one or two,
$R_1$ is hydrogen, halogen, $C_1$-$C_5$-alkyl, $C_2$-$C_5$-alkenyl, or a —Y—$R_6$ group,
$R_2$ is hydrogen, halogen, $C_1$-$C_5$-alkyl, $C_2$-$C_5$-alkenyl or $C_1$-$C_4$-haloalkyl, or a group —Y—$R_6$, —COO$R_7$, —NO$_2$ or —CO—N$R_8$—$R_9$,
$R_3$ is hydrogen, $C_1$-$C_4$-alkyl, $C_1$-$C_4$-alkoxy, $C_1$-$C_4$-alkylthio, $C_1$-$C_4$-haloalkyl, $C_1$-$C_4$-haloalkoxy, halogen or alkoxyalkyl having at most 4 carbon atoms,
$R_4$ is hydrogen, methyl or ethyl,
$R_5$ is hydrogen, $C_1$-$C_4$-alkyl, $C_1$-$C_3$-alkoxy, methoxymethyl, cyanomethyl or cyanoethyl,
$R_6$ and $R_7$ are each $C_1$-$C_5$-alkyl, $C_2$-$C_5$-alkenyl or $C_2$-$C_6$-alkynyl,
$R_8$ and $R_9$ independently of one another are each hydrogen $C_1$-$C_5$-alkyl, $C_2$-$C_5$-alkenyl or $C_2$-$C_6$-alkynyl, and
Y is oxygen, sulfur, or a sulfinyl or sulfonyl bridge.

19 Claims, No Drawings

N-PHENYLSULFONYL-N-TRIAZINYLUREAS

CROSS REFERENCE TO RELATED APPLICATIONS

This is a continuation-in-part of application Ser. No. 430,635 filed Sept. 30, 1982, now U.S. Pat. No. 4,579,584.

The present invention relates to novel N-phenylsulfonyl=N'-triazinylureas which have a herbicidal action and an action regulating plant growth, to compositions containing them as active ingredients, and also to the use thereof for combating weeds, particularly selectively in cultivated crops, or for regulating and reducing plant growth.

The N-phenylsulfonyl-N'-triazinylureas according to the invention correspond to the general formula I

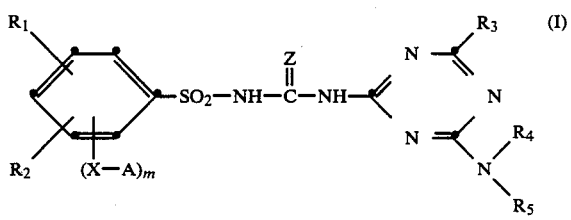

wherein
A is a $C_1-C_6$-halo alkyl group,
X is oxygen, sulfur, or a sulfinyl or sulfonyl bridge,
Z is oxygen or sulfur,
m is the number one or two,
$R_1$ is hydrogen, halogen, $C_1-C_5$-alkyl, $C_2-C_5$-alkenyl, or a —Y—$R_6$ group,
$R_2$ is hydrogen, halogen, $C_1-C_5$-alkyl, $C_2-C_5$-alkenyl or $C_1-C_4$-haloalkyl, or a group —Y—$R_6$, —COO$R_7$, —NO$_2$ or —CO—NR$_8$—R$_9$,
$R_3$ is hydrogen, $C_1-C_4$-alkyl, $C_1-C_4$-alkoxy, $C_1-C_4$-alkylthio, $C_1-C_4$-haloalkyl, $C_1-C_4$-haloalkoxy, halogen or alkoxyalkyl having at most 4 carbon atoms,
$R_4$ is hydrogen, methyl or ethyl,
$R_5$ is hydrogen, $C_1-C_4$-alkyl, $C_1-C_3$-alkoxy, methoxymethyl, cyanomethyl or cyanoethyl,
$R_6$ $R_7$ are each $C_1-C_5$-alkyl, or $C_2-C_6$-alkynyl,
$R_8$ and $R_9$ independently of one another are each hydrogen, $C_1-C_5$-alkyl, $C_2-C_5$-alkenyl or $C_2-C_6$-alkynyl, and
Y is oxygen, sulfur, or a sulfinyl or sulfonyl bridge, and the invention relates also to the salts of these compounds.

Urea compounds, triazine compounds and pyrimidine compounds having herbicidal activity are known in general. There have recently been described arylsulfamoyl-heterocyclyl-aminocarbamoyl compounds having a herbicidal action and an action regulating plant growth, for example in the European Patent Publications Nos. 9419 and 10560, or in the Dutch Patent Specification No. 121788.

Alkyl in the definitions is straight-chain or branched-chain alkyl, for example: methyl, ethyl, n-propyl, i-propyl, the four isomeric butyl groups, n-amyl, i-amyl, 2-amyl, 3amyl, n-hexyl or i-hexyl.

By alkoxy is meant: methoxy, ethoxy, n-propoxy, i-propoxy and the four isomeric butyloxy groups, in particular however methoxy, ethoxy or i-propoxy.

Examples of alkylthio are: methylthio, ethylthio, n-propylthio, i-propylthio and n-butylthio, but especially methylthio and ethylthio.

Examples of alkenyl groups are : vinyl, allyl, propropenyl, 1-propenyl, 1-butenyl, 2-butenyl, 3-butenyl, 1-isobutenyl, 2-isobutenyl, 1-pentenyl, 2-pentenyl, 3-pentenyl and 4-pentenyl, especially however vinyl, allyl and 4-pentenyl.

Halogen in the definitions, as well as in haloalkyl and haloalkoxy, is fluorine, chlorine and bromine, preferably fluorine and chlorine.

By haloalkyl or by haloalkyl moieties of the abovedefined substituents are accordingly meant for example: chloromethyl, fluoromethyl, difluoromethyl, trifluoromethyl, 2-chloroethyl, 2,2,2-trifluoroethyl, 1,1,2,2tetrafluoroethyl, pentafluoroethyl, 1,1,2-trifluoro-2chloroethyl, 2,2,2-trifluoro-1,1-dichloroethyl, pentachloroethyl, 3,3,3-trifluoropropyl, 2,2-dichloropropyl or 1,1,2,3,3,3-hexafluoropropyl, particularly however: fluoromethyl, chloromethyl, difluoromethyl and trifluoromethyl.

Alkynyl groups in the definitions of the above symbols are as a rule: propargyl, 2-butynyl and 3-butynyl, as well as isomeric pentynyl or hexynyl groups; the alkynyl group is preferably however propargyl or 2- or 3-butynyl.

The invention embraces also the salts which the compounds of the formula I can form with amines, alkali metal bases and alkaline-earth metal bases or quaternary ammonium bases. To be emphasised among the alkali metal and alkaline-earth metal hydroxides as salt formers are the hydroxides of lithium, sodium, potassium, magnesium or calcium, especially however those of sodium or potassium. Examples of amines suitable for forming salts are: primary, secondary and tertiary aliphatic and aromatic amines, such as methylamine, ethylamine, propylamine, i-propylamine, the four isomeric butylamines, dimethylamine, diethylamine, diethanolamine, dipropylamine, diisopropylamine, di-n-butylamine, pyrolidine, piperidine, morpholine, trimethylamine, triethylamine, tripropylamine, quinuclidine, pyridine, quinoline and i-quinoline, in particular however ethyl-, propyl, diethyl- or triethylamine, but especially isopropylamine and diethanolamine. Examples of quaternary ammonium bases are in general the cations of haloammonium salts, for example the tetramethylammonium cation, the trimethylbenzylammonium cation, the triethylbenzylammonium cation, the tetraethylammonium cation or the trimethylethylammonium cation, but also the ammonium cation.

Preferred compounds of the formula I are those in which
(a) X and
(b) Z are oxygen, and
(c) m is the number one,
(d) $R_4$ and $R_5$ together contain no more than 4 carbon atoms, and
(e) a group —X—A in the phenyl ring is in the 2-position with respect to the sulfonamide group.

By combination of the preferred features, there is formed a further preferred group of compounds of the formula I in which X and Y are oxygen, m is the number one, and $R_4$ and $R_5$ together contain no more than 4 carbon atoms, and the —X—A group in the phenyl ring occupies the 2-position with respect to the sulfonamide group.

A further preference within this group is where $R_1$ is hydrogen, and $R_2$ is hydrogen, halogen, methyl or $-COO-C_1-C_3$-alkyl.

Compounds among these to be emphasised are those in which $R_1$ and $R_2$ are hydrogen.

More especially preferred of these compounds are those wherein $R_3$ is methoxy, ethoxy, difluoromethoxy, 2,2,2-trifluoroethoxy, methyl, ethyl, fluoromethyl or chloromethyl $R_4$ is hydrogen, methyl or ethyl, and $R_5$ is methyl or ethyl.

The following individual compounds is preferred: N-(2-difluoromethoxyphenyl-sulfonyl)-N'-(4-dimethylamino-6-methoxy-1,3,5-triazin-2-yl)-urea.

The compounds of the formula I are produced in an inert organic solvent.

One process for obtaining the compounds of the formula I comprises reacting a phenylsulfonamide of the formula II

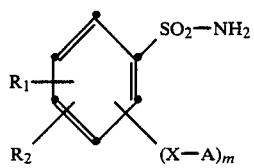

wherein A, $R_1$, $R_2$, X and m have the meanings defined under the formula I, in the presence of a base, with an N-triazinylcarbamate of the formula III

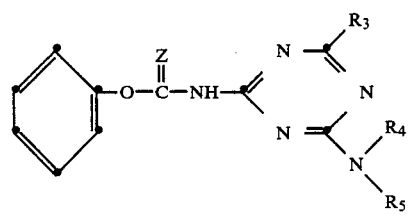

wherein $R_3$, $R_4$, $R_5$ and Z have the meanings defined under the formula I.

Compounds of the formula I are produced, using a second process, by reacting a phenylsulfonylisocyanate or -isothiocyanate of the formula IV

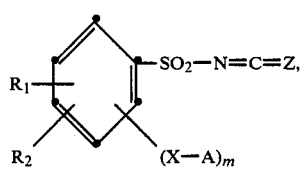

wherein A, $R_1$, $R_2$, m, X and Z have the meanings defined under the formula I, in the presence or absence of a base, with an amine of the formula V

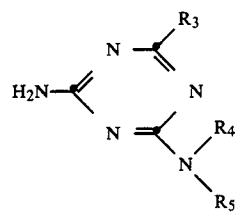

wherein $R_3$, $R_4$ and $R_5$ have the meanings defined under the formula I.

A further process for producing compounds of the formula I comprises reacting a sulfonamide of the above formula II, in the presence or absence of a base, with an isocyanate or isothiocyanate of the formula VI

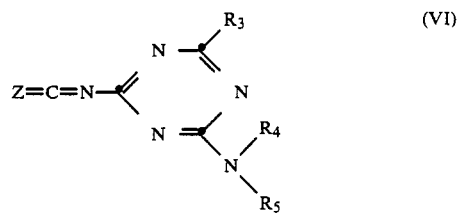

wherein $R_3$, $R_4$, $R_5$ and Z have the meanings defined under the formula I.

Furthermore, the compounds of the formula I can be obtained by reacting an N-phenylsulfonylcarbamate of the formula VII

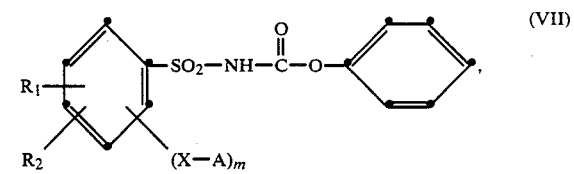

wherein A, $R_1$, $R_2$, m and X have the meanings defined under the formula I, with an amine of the formula V given above.

Finally, the compounds of the formula I are produced also by reacting a sulfonylurea of the formula VIII

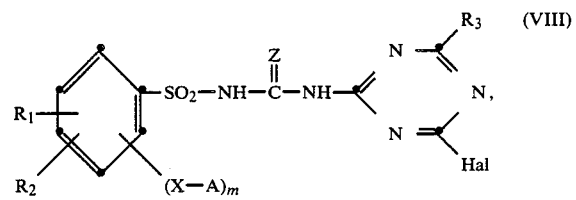

wherein A, $R_1$, $R_2$, $R_3$, X, Z and m having the meanings defined under the formula I, and Hal is chlorine or bromine, with an amine of the formula IX

wherein $R_4$ and $R_5$ have the meanings defined under the formula I.

The resulting ureas of the formula I can if desired be converted, by means of amines, alkali metal or alkaline-earth metal hydroxides or quaternary ammonium bases, into addition salts. This is effected for example by reaction with the equimolar amount of a base, and removal of the solvent by evaporation.

The starting materials of the formulae II, IV, VII, VIII and ortho-substituted hydroxyphenyl- or substituted ortho-hydroxyphenylsulfonamides of the formula X

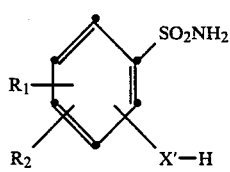

(X)

wherein $R_1$ and $R_2$ have the meanings defined under the formula I, and X' is oxygen or sulfur, are known, as starting products of specific sulfonamide representatives of the formula II, from the European Patent Application No. 44 807.

Some of the starting materials of the formulae III and VI are known, and new compounds of the formulae III and VI can be obtained by known methods from corresponding compounds of the formula V.

Novel fluoroalkoxy-aminotriazines of the formula V and their production, as well as the production of corresponding compounds of the formulae III and VI therefrom, are described in the U.S. Pat. No. 4,480,101. Other amines of the formula V are known and in part obtainable commercially; or they can be produced by known methods (cp. "The Chemistry of Heterocyclic Compounds", Vol. XIV, Interscience Publishers, New York, London).

Isocyanates of the formula V can be produced by reaction of amines of the formula V with oxalyl chloride in chlorinated hydrocarbons as solvent.

The starting materials of the formula IX are known, or can be produced by known methods.

The reactions to compounds of the formula I are advantageously performed in aprotic, inert, organic solvents, such as methylene chloride, tetrahydrofuran, acetonitrile, dioxane and toluene.

The reaction temperatures are preferably between −20° and +120° C. The reactions proceed in general slightly exothermically, and can be carried out at room temperature. For the purpose of shortening the reaction time or for initiating the reaction, it is advantageous to apply heat for a short time up to the boiling point of the reaction mixture. The reaction times can also-be shortened by the addition of some drops of a base or of isocyanate as a reaction catalyst.

The final products can be isolated by concentration by evaporation and/or by removal of the solvent by evaporation, and purified by recrystallisation or trituration of the solid residue in solvents in which they do not readily dissolve, such as ether, aromatic hydrocarbons or chlorinated hydrocarbons.

The active substances of the formula I are stable compounds, and the handling of them necessitates no special precautions being taken.

In smaller applied amounts, the compounds of the formula I are characterised by good selective growth-inhibiting and selective herbicidal properties, which render them excellently suitable for use in crops of useful plants, especially in crops of sugarcane, cereals, cotton, soya-bean, maize and rice. Also destroyed in some cases are weeds which hitherto could be dealt with only be the use of total herbicides.

The mode of action of these active substances is unusual. Many are capable of being translocated, that is to say, they are taken up by the plant and transported to other locations, where they produce the desired effect. It is thus possible for example by surface treatment of perennial weeds to destroy them at their roots. The novel compounds of the formula I are effective in applied amounts which are very small compared with the amounts required to obtain the same effect using other herbicides and plant-growth regulators.

The compounds of the formula I also have excellent properties for regulating plant growth, the effects of which can be an increase in the yield of cultivated plants or of harvested crops. Many compounds of the formula I also exhibit an action reducing plant growth to an extent dependent on the concentration. Both monocotyledons and dicotyledons are impaired in their growth.

Thus, for example, the leguminosae frequently planted as cover crops in agriculture in tropical regions can be selectively inhibited in their growth by the compounds of the formula I, the result being that soil erosion between the cultivated plants is prevented, without the cover crops being able to compete with the main cultivated crop.

A reduction of the vegetative growth enables in the case of many cultivated plants the crop density to be increased, so that higher yields for the same area of land can be achieved.

An additional factor contributing to the increase in yield with the use of growth inhibitors is that the formation of blossom and fruit benefits to a greater extent from the nutritive substances, because the vegetative growth is restricted.

In the case of monocotyledonous plants, for example grasses, or cultivated plants such as cereals, a reduction of vegetative growth is sometimes desirable and advantageous. A reduction of growth of this kind is of economical interest with regard to, among other things, grasses, for as a consequence it is possible to reduce the frequency of the cutting of grass in ornamental gardens, parks and sports grounds, or along the verges of highways. Of importance also is the inhibition of the growth of herbaceous and ligneous plants at the edges of roads and in the vicinity of overhead transmission lines, or quite generally in areas where a strong growth is undesirable.

Also important is the application of growth regulators for reducing the growth in height of cereals, since a shortening of the stems lessens or completely removed the danger of the snapping off (flattening) of the plants before harvesting. Furthermore, growth regulators can result in a strengthening of the stems of cereal crops, a further factor acting to prevent bending of the stems, of the plants.

The compounds of the formula I are likewise suitable for preventing the sprouting of stored potatoes. Shoots frequently form on potatoes being stored during the winter, and these shoots cause shrinkage, loss in weight and rotting.

With larger applied amounts of active substance, all the tested plants are impaired in their development to the extent that they wither.

The present invention relates also to herbicidal and plant-growth-regulating compositions containing a novel active ingredient of the formula I, and also to processes for the pre- and post-emergence combating of weeds, and for the reduction of growth of monocotyledonous and dicotyledonous plants, particularly that of grasses, tropical cover crops and side shoots of tobacco plants.

The compounds of the formula I are used either in an unmodified form or preferably in compositions, together with auxiliaries customarily employed in formulation practice, and are thus processed, in a known manner, for example into the form of emulsion concentrates, directly sprayable or dilutable solutions, diluted emulsions, wettable powders, soluble powders, dusts or granulates, and also encapsulations in for example polymeric substances. The application processes, such as spraying, atomising, dusting, scattering or pouring, and likewise the type of composition, are selected to suit the objects to be achieved and the given conditions.

The formulations, that is to say, the compositions or preparations containing the active ingredient of the formula I and optionally a solid or liquid additive, are produced in a known manner, for example by the intimate mixing and/or grinding of the active ingredients with extenders, such as with solvents, solid carriers and optionally surface-active compounds (tensides).

Suitable solvents are: aromatic hydrocarbons, preferably the fractions $C_8$ to $C_{12}$, such as xylene mixtures or substituted naphthalenes, phthalic esters, such as dibutyl- or dioctylphthalate, aliphatic hydrocarbons, such as cyclohexane or paraffins, alcohols and glycols, as well as ethers and esters thereof, such as ethanol, ethylene glycol, ethylene glycol monomethyl or -ethyl ethers, ketones, such as cyclohexanone, strongly polar solvents, such as N-methyl-2-pyrrolidone, dimethylsulfoxide or dimethylformaide, as well as optionally epoxidised vegetable oils, such as epoxidised coconut oil or soybean oil; or water.

The solid carriers used, for example for dusts and dispersible powders, are as a rule natural mineral fillers, such as calcite, talcum, kaolin, montmorillonite or attapulgite. In order to improve the physical properties, it is also possible to add highly dispersed silicic acid or highly dispersed absorbent polymers. Suitable granulated adsorptive carriers are porous types, for example pumice ground brick, sepiolite or bentonite; and suitable nonsorbent carriers are materials such as calcite or sand. There can also be used a great number of pre-granulated materials of inorganic or organic nature, such as in particular dolomite or ground plant residues.

Suitable surface-active compounds are, depending on the nature of the active substance of the formula I to be formulated, nonionic, cationic and/or anionic tensides having good emulsifying, dispersing and wetting properties. By 'tensides' are also meant mixtures of tensides.

Suitable anionic tensides are both so-called water-soluble soaps as well as water-soluble, synthetic, surface-active compounds.

Soaps which are applicable are the alkali metal, alkaline-earth metal or optionally substituted ammonium salts of higher fatty acids ($C_{10}$–$C_{22}$), for example the Na or K salts of oleic or stearic acid, or of natural fatty acid mixtures, which can be obtained for example from coconut oil or tallow oil. Also to be mentioned are fatty acid-methyl-taurine salts.

So-called synthetic tensides are however more frequently used, particularly fatty sulfonates, fatty sulfates, sulfonated benzimidazole derivatives or alkylarylsulfonates. The fatty sulfonates or sulfates are as a rule in the form of alkali metal, alkaline-earth metal or optionally substituted ammonium salts, and contain an alkyl group having 8 to 22 C atoms, 'alkyl' including also the alkyl moiety of acyl groups, for example the Na or Ca salt of ligninsulfonic acid, of dodecylsulfuric acid ester or of a fatty alcohol sulfate mixture produced from natural fatty acids; included among these are also the salts of sulfuric acid esters and sulfonic acids of fatty alcohol ethylene oxide adducts. The sulfonated benzimidazole derivatives preferably contain 2 sulfonic acid groups and a fatty acid group having 8-22 C atoms. Alkylarylsulfonates are for example the Na, Ca or triethanolamine salts of dodecylbenzenesulfonic acid, of dibutylnaphthalenesulfonic acid or of a naphthalenesulfonic acid-formaldehyde condensation product. Also suitable are corresponding phosphates, for example salts of the phosphoric ester of a p-nonylphenol-(4–14)-ethylene oxide adduct.

Suitable nonionic tensides are in particular polyglycol ether derivatives of aliphatic or cycloaliphatic alcohols, saturated or unsaturated fatty acids and alkylphenols, which can contain 3 to 30 glycol ether groups and 8 to 20 carbon atoms in the (aliphatic) hydrocarbon radical and 6 to 18 carbon atoms in the alkyl moiety of the alkylphenols.

Further suitable nonionic tensides are the water-soluble polyethylene oxide adducts, which contain 20 to 250 ethylene glycol ether groups and 10 to 100 propylene glycol ether groups, with polypropylene glycol, ethylenediaminopolypropylene glycol and alkylpolypropylene glycol having 1 to 10 carbon atoms in the alkyl chain. The compounds mentioned usually contain 1 to 5 ethylene glycol units per propylene glycol unit. Examples of nonionic tensides which may be mentioned are: nonylphenol TM polyethoxyethanols, castor oil polyglycol ethers, polypropylene/polyethyleneoxy adducts, tributylphenoxypolyethoxyethanol, polyethylene glycol and octylphenoxypolyethoxyethanol. Suitable also are fatty acid esters of polyoxyethylenesorbitan, such as polyoxyethylenesorbitan-trioleate.

In the case of the cationic tensides, they are in particular quaternary ammonium salts which contain as N-substituents at least one alkyl group having 8 to 22 C atoms and, as further substituents, lower, optionally halogenated alkyl, benzyl or lower hydroxyalkyl groups. The salts are preferably in the form of halides, methyl sulfates or ethyl sulfates, for example stearyltrimethylammonium chloride or benzyldi(2-chloroethyl)ethylammonium bromide.

The tensides customarily used in formulation practice are described, inter alia, in the following publications: "Mc Cutcheon's Detergents and Emulsifiers Annual" MC Publishing Corp., Ridgewood, N.J., 1979; and Sisley and Wood, "Encyclopedia of Surface Active Agents", Chemical Publishing Co., Inc. New York, 1964.

The agrochemical preparations contain as a rule 0.1 to 95%, especially 0.1 to 80%, of active ingredient of the formula I, 1 to 99.9% of a solid or liquid additive, and 0 to 25%, particularly 0.1 to 25%, of a tenside.

Preferred formulations are made up in particular as follows (%=percent by weight):

| Emulsifiabe concentrates | |
| --- | --- |
| active ingredient | 1 to 20%, preferably 5 to 10% |
| surface active agent | 5 to 30%, preferably 10 to 20% |
| liquid carrier | 50 to 94%, preferably 70 to 85%. |
| Dusts | |
| active ingredient | 0.1 to 10%, preferably 0.1 to 1% |
| solid carrier | 99.9 to 90%, preferably 99.9 to 99%. |
| Suspension concentrates | |
| active ingredient | 5 to 75%, preferably 10 to 50% |
| water | 94 to 25%, preferably 90 to 30% |
| surface-active agent | 1 to 40%, preferably 2 to 30%. |
| Wettable powders | |
| active ingredient | 0.5 to 90%, preferably 1 to 80% |
| surface-active agent 0.5 to 20%, preferably 1 to 15% | |

|  | -continued |
|---|---|
| solid carrier | 5 to 95%, preferably 15 to 90%. |
| Granulates |  |
| active ingredient | 0.5 to 30%, preferably 3 to 15% |
| solid carrier | 99.5 to 70%, preferably 97 to 85%. |

Whereas commercial products are preferably in the form of concentrated compositions, the compositions employed by the end-user are as a rule diluted. The preparations can for application be diluted down to 0.001% of active ingredient. The applied amounts are usually 0.001 to 10 kg, preferably 0.025 to 5 kg, of active substance per hectare.

The compositions can also contain additives such as stabilizers, antifoaming agents, viscosity regulators, binders and adhesives, as well as fertilizers or other active substances for obtaining special effects.

In the following Examples, the temperatures are given in degrees Centigrade (°C.), and pressures in millibars (mb).

PRODUCTION EXAMPLES

EXAMPLE 1

N-(2-Difluoromethoxyphenyl-sulfonyl)-N'-(4-dimethylamino-6-methoxy-1,3,5-triazin-2-yl)-urea (a) To the suspension of 80.3 g of 2-amino-4-chloro-6-methoxy-1,3,5-triazine in 400 ml of absolute dioxane are added dropwise, within 10 minutes, 124.6 g of 2-difluoromethoxy-sulfonylisocyanate in 100 ml of dioxane. The reaction mixture is heated for 3 hours at 90°–100° C. After cooling and concentrating the reaction solution by evaporation, the yield is 180 g of N-(2-difluoromethoxyphenyl-sulfonyl)-N'-(4-chloro-6-methoxy-1,3,5-triazin-2-yl)urea, m.p. 167°–168° C.

(b) 3.0 g of dimethylamine are introduced at 20°–30° C., with cooling, into a solution of 8.2 g of N-(2-difluoromethoxyphenyl-sulfonyl)-N'-(4-chloro-6-methoxy-1,3,5-triazin-2-yl)-urea in 80 ml of dioxane. After the formed suspension has been stirred for a further 30 minutes, it is taken up in 500 ml of 0.1 N hydrochloric acid, and the product which has precipitated is separated by filtration; yield: 7.7 g of N-(2-difluoromethoxyphenyl-sulfonyl)-N'-(4-dimethylamino-6-methoxy-1,3,5-triazin-2-yl)-urea, m.p. 171°–172° C.

EXAMPLE 2

N-(2-Difluoromethoxyphenyl-sulfonyl)-N'-(4-tert-butylamino-6-methoxy-1,3,5-triazin-2-yl)-urea A mixture of 5.0 g of 2-difluoromethoxyphenyl-sulfonylisocyanate and 4.0 g of 2-amino-4-tert-butylamino-6-methoxy-1,3,5-triazine is stirred in 60 ml of absolute dioxane for 3 hours at 70°–80° C. After filtration of the hot reaction mixture through active charcoal, 6.9 g of N-(2-difluoromethoxyphenyl-sulfonyl)-N'-(4-tert-butylamino-6-methoxy-1,3,5-triazin-2-yl)-urea, m.p. 213°–214° C., crystallise out on cooling of the solution.

The final products listed in the subsequent Tables are obtained in an anlogous manner.

TABLE 1

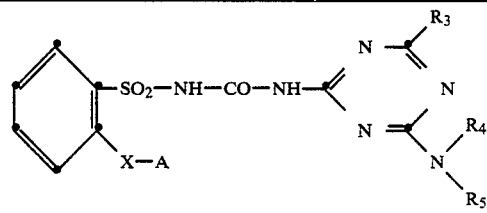

| No. | A | X | $R_3$ | $R_4$ | $R_5$ | m.p. °C. |
|---|---|---|---|---|---|---|
| 1 | $CHF_2$ | O | $OCH_3$ | $CH_3$ | $-CH_2-CN$ |  |
| 2 | $CHF_2$ | O | $OCH_3$ | $CH_3$ | $-CH_2-CH_2-CN$ | 172–173 |
| 3 | $CHF_2$ | O | $OC_2H_5$ | $CH_3$ | $CH_3$ |  |
| 4 | $CHF_2$ | O | $-OCH_2-CF_3$ | $CH_3$ | $OCH_3$ |  |
| 5 | $CHF_2$ | O | $-OCH_2-CF_3$ | $CH_3$ | $CH_3$ | 172–173 |
| 6 | $CHF_2$ | O | $-OCH_2-CF_3$ | $CH_3$ | $OCH_3$ |  |
| 7 | $CHF_2$ | O | $CH_3$ | $CH_3$ | $CH_3$ | 193–194 |
| 8 | $CHF_2$ | S | $OCH_3$ | $CH_3$ | $OCH_3$ |  |
| 9 | $CHF_2$ | S | $OCH_3$ | $C_2H_5$ | $OCH_3$ |  |
| 10 | $CHF_2$ | S | $OCH_3$ | $CH_3$ | $OCH_3$ |  |
| 11 | $CHF_2$ | S | $OCH_3$ | $CH_3$ | $-CH_2-CH_2-CN$ |  |
| 12 | $CHF_2$ | S | $OCH_3$ | $CH_3$ | $-CH_2-CN$ |  |
| 13 | $CHF_2$ | S | $OC_2H_5$ | $CH_3$ | $CH_3$ |  |
| 14 | $CHF_2$ | S | $-OCH_2-CF_3$ | $CH_3$ | $CH_3$ |  |
| 15 | $CHF_2$ | S | $-OCH_2-CF_3$ | $CH_3$ | $OCH_3$ |  |
| 16 | $CHF_2$ | S | $OC_2H_5$ | $CH_3$ | $OCH_3$ |  |
| 17 | $-CH_2-CH_2Cl$ | O | $OCH_3$ | $CH_3$ | $OCH_3$ |  |
| 18 | $-CH_2-CH_2Cl$ | O | $OCH_3$ | $C_2H_5$ | $OCH_3$ |  |
| 19 | $-CH_2-CH_2Cl$ | O | $OCH_3$ | $C_2H_5$ | $CH_3$ |  |
| 20 | $-CH_2-CH_2Cl$ | O | $OCH_3$ | $CH_3$ | $-CH_2-CH_2-CN$ |  |
| 21 | $-CH_2-CH_2Cl$ | O | $OCH_3$ | $CH_3$ | $-CH_2-CN$ |  |
| 22 | $-CH_2-CH_2Cl$ | O | $OC_2H_5$ | $CH_3$ | $CH_3$ |  |
| 23 | $-CH_2-CH_2Cl$ | O | $-OCH_2-CF_3$ | $CH_3$ | $CH_3$ |  |
| 24 | $-CH_2-CH_2Cl$ | O | $-OCH_2-CF_3$ | $CH_3$ | $OCH_3$ |  |
| 25 | $-CH_2-CH_2Cl$ | O | $OC_2H_5$ | $CH_3$ | $OCH_3$ |  |
| 26 | $-CF_2-CHF_2$ | O | $OCH_3$ | $CH_3$ | $OCH_3$ |  |
| 27 | $-CF_2-CHF_2$ | O | $OCH_3$ | $C_2H_5$ | $OCH_3$ |  |
| 28 | $-CF_2-CHF_2$ | O | $OCH_3$ | $C_2H_5$ | $CH_3$ |  |
| 29 | $-CF_2-CHF_2$ | O | $OCH_3$ | $CH_3$ | $-CH_2-CH_2-CN$ |  |
| 30 | $-CF_2-CHF_2$ | O | $OCH_3$ | $CH_3$ | $-CH_2-CN$ |  |
| 31 | $-CF_2-CHF_2$ | O | $OC_2H_5$ | $CH_3$ | $CH_3$ |  |
| 32 | $-CF_2-CHF_2$ | O | $-OCH_2-CF_3$ | $CH_3$ | $CH_3$ |  |

TABLE 1-continued

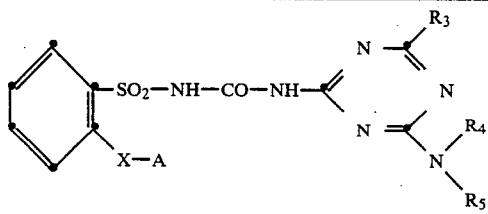

| No. | A | X | $R_3$ | $R_4$ | $R_5$ | m.p. °C. |
|---|---|---|---|---|---|---|
| 33 | —$CF_2$—$CHF_2$ | O | —$OCH_2$—$CF_3$ | $CH_3$ | $OCH_3$ | |
| 34 | —$CF_2$—$CHF_2$ | O | $OC_2H_5$ | $CH_3$ | $OCH_3$ | |
| 35 | $CF_3$ | O | $OCH_3$ | $CH_3$ | $OCH_3$ | |
| 36 | $CF_3$ | O | $OCH_3$ | $CH_3$ | $CH_3$ | 182–183 |
| 37 | $C_2F_5$ | O | $OCH_3$ | $CH_3$ | $CH_3$ | 175–176 |
| 38 | $C_2F_5$ | O | $OCH_3$ | $CH_3$ | $OCH_3$ | |
| 39 | —$CF_2$—CHFCl | O | $OCH_3$ | $CH_3$ | $CH_3$ | |
| 40 | —$CF_2$—CHFCl | O | $OCH_3$ | $CH_3$ | $OCH_3$ | |
| 41 | $CHF_2$ | O | $OCH_3$ | $CH_3$ | $CH_3$ | 171–172 |
| 42 | $CHF_2$ | O | $SCH_3$ | $CH_3$ | $CH_3$ | 184–185 |
| 43 | $CHF_2$ | S | $SCH_3$ | $CH_3$ | $CH_3$ | |
| 44 | $CHF_2$ | O | i-$C_3H_7$ | $CH_3$ | $CH_3$ | 150–153 |
| 45 | $CHF_2$ | S | i-$OC_3H_7$ | $CH_3$ | $CH_3$ | 178–180 |
| 46 | $CHF_2$ | O | $OCH_3$ | H | H | >250 |
| 47 | $CHF_2$ | O | $OCH_3$ | H | t-$C_4H_9$ | 213–214 |
| 48 | $CHF_2$ | O | $OCH_3$ | H | $C_2H_5$ | 191–192 |
| 49 | $CHF_2$ | O | $OCH_3$ | H | $CH_3$ | 188–190 |
| 50 | $CHF_2$ | S | $OCH_3$ | $CH_3$ | $CH_3$ | 188–190 |
| 51 | $CHF_2$ | O | $OCH_3$ | $CH_3$ | $OCH_3$ | 122 (decomp) |
| 52 | $CHF_2$ | O | Cl | $CH_3$ | $CH_3$ | 199–200 |
| 53 | —$CH_2$—$CH_2Cl$ | O | $OCH_3$ | $CH_3$ | $CH_3$ | 181–182 |
| 54 | —$CF_2$—$CHF_2$ | O | $OCH_3$ | $CH_3$ | $CH_3$ | 169–170 |
| 55 | $CHF_2$ | O | $OCH_3$ | $CH_3$ | $C_2H_5$ | 172–173 |
| 56 | —$CH_2$—$CH_2Cl$ | O | $OCH_3$ | $CH_3$ | H | |
| 57 | —$CF_2$—$CHF_2$ | O | $OCH_3$ | $CH_3$ | H | |
| 58 | $CF_3$ | O | $OCH_3$ | $CH_3$ | H | |
| 59 | —$C_2F_5$ | O | $OCH_3$ | $CH_3$ | H | |
| 60 | —$CF_2$—CHFCl | O | $OCH_3$ | $CH_3$ | H | |
| 61 | $CHF_2$ | O | Cl | $CH_3$ | $CH_3$ | 199–200 |
| 62 | —$CH_2$—$CH_2Cl$ | O | $OCH_3$ | $CH_3$ | $CH_3$ | 181–182 |
| 63 | —$CF_2$—$CHF_2$ | O | $OCH_3$ | $CH_3$ | $CH_3$ | 169–170 |
| 64 | $CHF_2$ | O | $OCH_3$ | $CH_3$ | —$CH_2CH_3$ | 172–173 |
| 65 | $CHF_2$ | S | $OCH_3$ | $CH_3$ | H | 197–198 |
| 66 | $CHF_2$ | O | $OCHF_2$ | $CH_3$ | $CH_3$ | |

TABLE 2

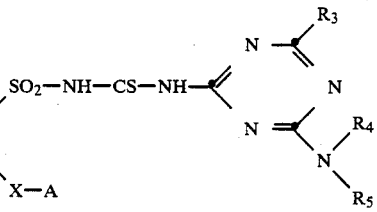

| No. | A | X | $R_3$ | $R_4$ | $R_5$ | m.p. °C. |
|---|---|---|---|---|---|---|
| 101 | $CHF_2$ | O | $OCH_3$ | $CH_3$ | $CH_3$ | |
| 102 | $CHF_2$ | O | $OCH_3$ | $CH_3$ | $OCH_3$ | |
| 103 | $CHF_2$ | S | $OCH_3$ | $CH_3$ | $OCH_3$ | |
| 104 | $CHF_2$ | S | $OCH_3$ | $CH_3$ | $CH_3$ | |

TABLE 3

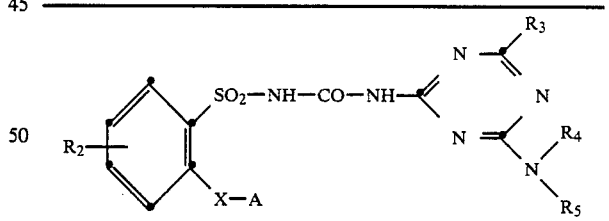

| No. | A | X | $R_2$ | $R_3$ | $R_4$ | $R_5$ | m.p. °C. |
|---|---|---|---|---|---|---|---|
| 201 | $CHF_2$ | O | 5-F | $OCH_3$ | $CH_3$ | $CH_3$ | 169–172 |
| 202 | $CHF_2$ | O | 5-F | $OCH_3$ | $CH_3$ | $OCH_3$ | |
| 203 | $CHF_2$ | O | 5-Cl | $OCH_3$ | $CH_3$ | $CH_3$ | 171–172 |
| 204 | $CHF_2$ | O | 5-Cl | $OCH_3$ | $CH_3$ | $OCH_3$ | |
| 205 | $CHF_2$ | O | 6-Cl | $OCH_3$ | $CH_3$ | $CH_3$ | 149–151 |
| 206 | $CHF_2$ | O | 6-Cl | $OCH_3$ | $CH_3$ | $OCH_3$ | |
| 207 | $CHF_2$ | O | 5-$CHF_2$ | $OCH_3$ | $CH_3$ | $CH_3$ | |
| 208 | $CHF_2$ | O | 5-$CHF_2$ | $OCH_3$ | $CH_3$ | $OCH_3$ | |
| 209 | $CHF_2$ | O | 5-$COOCH_3$ | $OCH_3$ | $CH_3$ | $CH_3$ | |
| 210 | $CHF_2$ | O | 5-$COOCH_3$ | $OCH_3$ | $CH_3$ | $OCH_3$ | |
| 211 | $CHF_2$ | O | 6-F | $OCH_3$ | $CH_3$ | $CH_3$ | |
| 212 | $CHF_2$ | O | 6-F | $OCH_3$ | $CH_3$ | $OCH_3$ | |

FORMULATION EXAMPLES

EXAMPLE 3

Formulation Examples for active ingredients of the formula I (%=percent by weight)

| (a) Wettable powder | (a) | (b) | (c) |
|---|---|---|---|
| active ingredient | 20% | 60% | 0.5% |
| sodium lignin sulfonate | 5% | 5% | 5% |
| sodium lauryl sulfate | 3% | — | — |
| sodium diisobutylnaphthalene sulfonate | — | 6% | 6% |
| octylphenolpolyethylene glycol ether (7–8 mols of ethylene oxide) | — | 2% | 2% |
| highly dispersed silicic acid | 5% | 27% | 27% |
| kaolin | 67% | — | — |
| sodium chloride | — | — | 59.5% |

The active ingredient is well mixed with the additives and ground in a suitable mill. There are obtained wettable powders which can be diluted with water to give suspensions of the concentration desired.

| (b) Emulsion concentrate | (a) | (b) |
|---|---|---|
| active ingredient | 10% | 1% |
| octylphenolpolyethylene glycol ether (4–5 mols of ethylene oxide) | 3% | 3% |
| calcium dodecyl benzene sulfonate | 3% | 3% |
| castor oil polyglycol ether (36 mols of ethylene oxide) | 4% | 4% |
| cyclohexanone | 30% | 10% |
| xylene mixture | 50% | 79% |

Emulsions of the concentration desired can be obtained from this concentrate by dilution with water.

| (c) Dusts | (a) | (b) |
|---|---|---|
| active ingredient | 0.1% | 1% |
| talcum | 99.9% | — |
| kaolin | — | 99% |

Dusts ready for use are obtainer by mixing the active-ingredient with the carriers, and grinding the mixture in a suitable mill.

| (d) Extruder granulate | (a) | (b) |
|---|---|---|
| active ingredient | 10 | 1% |
| sodium lignin sulfonate | 2% | 2% |
| carboxymethylcellulose | 1% | 1% |
| kaolin | 87% | 96% |

The active ingredient is mixed with the additives, and the mixture is then ground and moistened with water. It is extruded and subsequently dried in a stream of air.

| (e) Coated granulate | |
|---|---|
| active ingredient | 3% |
| polyethylene glycol (MG 200) | 3% |
| kaolin | 94% |

The finely ground active ingredient is uniformly applied, in a mixer, to the kaolin moistened with polyethylene glycol. Non-dusty coated granulates are obtained in this manner.

| (f) Suspension concentrate | (a) | (b) |
|---|---|---|
| active ingredient | 40% | 5% |
| ethylene glycol | 10% | 10% |
| nonylphenolpolyethylene glycol ether (15 mols of ethylene oxide) | 6% | 1% |
| sodium lignin sulfonate | 10% | 5% |
| carboxymethylcellulose | 1% | 1% |
| 37% aqueous formaldehyde solution | 0.2% | 0.2% |
| silicone oil in the form of a 75% aqueous emulsion | 0.8% | 0.8% |
| water | 32% | 77%. |

The finely ground active ingredient is intimately mixed with the additives. There is thus obtained a suspension concentrate from which can be produced, by dilution with water, suspensions of the concentration desired.

| (g) Salt solution | |
|---|---|
| active ingredient | 5% |
| isopropylamine | 1% |
| octylphenolpolyethylene glycol ether (78 mols of ethylene oxide) | 3% |
| water | 91%. |

BIOLOGICAL EXAMPLES

EXAMPLE 4

Herbicidal action before emergence of the plants

Plastics pots are filled with expanded vermiculite (density: 0.135 g/cm$^3$, water-absorption capacity: 0.565 l/l). After saturation of the non-adsorptive vermiculite with an aqueous active-substance emulsion in deionised water, which contains the active ingredient at a concentration of 70.8 ppm, seeds of the following plants are sown on the surface: Nasturtium officinalis, Agrostis tenuis, Stellaria media and Digitaria sanguinalis. The test vessels are subsequently kept in a climatic chamber at 20° C., with an illumination of about 20 k lux and a relative humidity of 70%. During the germination phase of 4 to 5 days, the pots are covered over with light-permeable material in order to raise the local air humidity and watered with deionised water. After the 5th day, 0.5% of a commercial liquid fertiliser (®Greenzit) is added to the water. The test is evaluated 12 days after sowing, and the effect on the test plants assessed according to the following scale of ratings:

1 plants have not germinated or are totally destroyed
2–3 very strong action
4–6 medium action
7–8 weak action
9 no action (as untreated control plants)

PRE-EMERGENCE ACTION

Concentration of the active-ingredient emulsion: 70.8 ppm

| Active ingredient No | Test plant | | | |
|---|---|---|---|---|
| | Nasturtium | Stellaria | Agrostis | Digitaria |
| 2 | 2 | — | — | — |
| 5 | 1 | 1 | 1 | — |
| 7 | 3 | — | — | — |
| 36 | 1 | 2 | 1 | 2 |
| 37 | 2 | 2 | 1 | — |
| 42 | 2 | — | — | — |

-continued

| Active ingredient No | Test plant | | | |
|---|---|---|---|---|
| | Nasturtium | Stellaria | Agrostis | Digitaria |
| 44 | 6 | — | — | — |
| 46 | 2 | — | — | — |
| 47 | 5 | — | — | — |
| 48 | 2 | — | — | — |
| 49 | 3 | — | — | — |
| 50 | 2 | — | — | — |
| 51 | 2 | — | — | — |
| 62 | 1 | 1 | 1 | 1 |
| 63 | 1 | 1 | 1 | 2 |
| 64 | 2 | — | — | — |
| 65 | 2 | 2 | 2 | 2 |
| 66 | 1 | 1 | 1 | 1 |
| 103 | 1 | 1 | 1 | 1 |
| 201 | 1 | 2 | 1 | 2 |

—: not tested

EXAMPLE 5

Herbicidal action after emergence of the plants (contact action)

A number of weeds and cultivated plants, both monocotyledonous and dicotyledonous, are sprayed after emergence, in the 4- to 6-leaf stage, with an aqueous active-ingredient dispersion in dosages of 4 kg of active ingredient per hectare, and then kept at 24° to 26° C with 45–60% relative humidity. The test results are evaluated 15 days after the treatment, and an assessment is made according to the same scale of ratings as in the preemergence test.

POST-EMERGENCE ACTION

Applied amount: 4 kg of active ingredient per hectare

| Comp. No. | Avena | Setaria | Lolium | Solanum | Sinapis | Stellaria | Phascolus |
|---|---|---|---|---|---|---|---|
| 42 | 6 | 5 | 4 | 2 | 2 | 3 | 3 |
| 44 | 9 | 9 | 5 | 2 | 2 | 3 | 3 |
| 51 | 2 | 3 | 2 | 2 | 2 | 2 | 3 |

EXAMPLE 6

Reduction in growth of tropical leguminous cover crops

The test plants (Centrosema plumieri and Centrosema pubescens) are cultivated to the fully grown stage, and then cut back to a height of 60 cm. After 7 days, the the active ingredient is sprayed on in the form of an aqueous emulsion. The test plants are maintained at 70% relative humidity and with 6000 lux of artificial light, 14 hours per day, at temperatures of 27° C. by day and 21° C. by night. The test results are assessed 4 weeks after application of the emulsion. The new growth occurring compared with that on the control plants is estimated and weighed, and the phytotoxicity is evaluated. The plants treated with the active ingredients of the formula I show in this test a clear reduction in new growth (less than 20% of the new growth occurring on untreated control plants), without the test plants having suffered damage.

EXAMPLE 7

Regulation of growth of soya-bean plants

Soya-beans of the "Hark" variety are sown in plastic containers holding a soil/peat/sand mixture in the ratio of 6:3:1, and are placed into a climatic chamber. By optimum choice of temperature, illumination, fertiliser addition and watering, the plants develop over about 5 weeks into the 5–6 trifoliate stage. At this point, the plants are sprayed until thoroughly dripping wet with the aqueous liquor of an active ingredient of the formula I, the active-ingredient concentration being up to 100 g of active ingredient per hectare. An assessment of the results is made about 5 weeks after application of the active ingredient. The active ingredients of the formula I produce a marked increase in the number and in the weight of the pods on the leading shoots compared with the number and weight of pods on the untreated control plants.

EXAMPLE 8

Reduction of growth of cereals

The cereal varieties Hordeum vulgare (spring barley) and Secale (spring rye) are sown in plastics pots containing sterilised soil in a greenhouse, and watered as required. The young shoots are sprayed, about 21 days after sowing, with the aqueous spray liquor of an active ingredient of the formula I. The amount applied is up to 100 g of active ingredient per hectare, and 21 days after application, the growth of the cereals is assessed. The treated plants show a reduction in the extent of new growth compared with that on the untreated control plants (60–90% of the new growth on the control plants), and also in part an increase in the diameter of the stems of the plants.

EXAMPLE 9

Reduction of growth of grasses

The grasses Lolium perenne, Poa pratensis, Festuca ovina, Dactylis glomerata and Cynodon dactylon are sown, in a greenhouse, in plastics dishes containing a soil/peat/sand mixture (6:3:1), and watered as required. The emerged grasses are cut back weekly to a height of 4 cm. and are sprayed, about 50 days after sowing and one day after the final cutting, with the aqueous spray liquor of the active ingredient of the formula I. The amount of active ingredient corresponds, when converted, to up to 100 g per hectare. The growth of the grasses is assessed 21 days after application.

The compounds of the formula I effect a reduction of new growth of around 10–30%, compared with the new growth of the untreated control grasses.

What is claimed is:

1. A compound selected from the group consisting of a triazinylsulfonylurea of the formula:

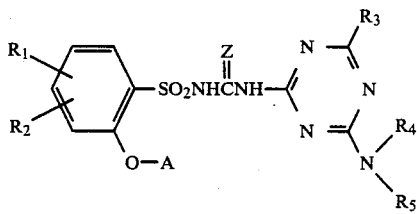

wherein Z is O or S;
A is haloalkyl of 1 to 6 carbon atoms;
$R_1$ is hydrogen, halo, alkyl of 1 to 5 carbon atoms, alkenyl of 2 to 5 carbon atoms, or $R_6$—Y— in which
 Y is O, S, SO, or $SO_2$ and
 $R_6$ is alkyl of 1 to 5 carbon atoms, alkenyl of 2 to 5 carbon atoms, or alkynyl of 2 to 6 carbon atoms;
$R_2$ is hydrogen, halo, alkyl of 1 to 5 carbon atoms, alkenyl of 2 to 5 carbon atoms, haloalkyl of 1 to 4 carbon atoms, $R_5$—Y—, nitro, $R_7OCO$—, or $R_8R_9NCO$—, in which Y and $R_6$ are as defined above;
$R_7$ is an alkyl of 1 to 5 carbon atoms, alkenyl of 2 to 5 carbon atoms, or alkynyl of 2 to 6 carbon atoms; and
each of $R_8$ and $R_9$ is independently hydrogen, alkyl of 1 to 5 carbon atoms, alkenyl of 2 to 5 carbon atoms of alkynyl of 2 to 6 carbon atoms;
$R_3$ is hydrogen, halo, alkyl of 1 to 4 carbon atoms, alkoxy of 1 to 4 carbon atoms, alkylthio of 1 to 4 carbon atoms, haloalkyl of 1 to 4 carbon atoms, haloalkoxy of 1 to 4 carbon atoms, or alkoxyalkyl of up to 4 carbon atoms;
$R_4$ is hydrogen, methyl, or ethyl; and
$R_5$ is hydrogen, alkyl of 1 to 4 carbon atoms, alkoxy of 1 to 3 carbon atoms, methoxymethyl, cyanomethyl, or cyanoethyl; and the salts thereof.

2. A compound according to claim 1 and selected from the group consisting of a triazinylsulfonylurea of the formula:

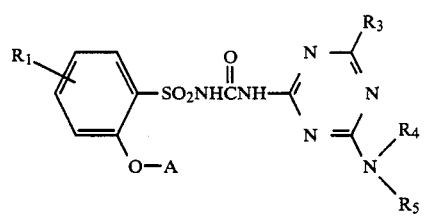

wherein A is difluoromethyl, trifluoromethyl, 1,1,2,2,-tetrafluoroethyl, pentafluoroethyl, 2-chloro-1,1,2-trifluoroethyl, or 2-chloroethyl;

$R_3$ is chloro, methyl, ethyl, isopropyl, methoxy, ethoxy, isopropoxy, methylthio, difluoromethoxy, or 2,2,2-trifluoroethoxy;
$R_4$ is hydrogen, methyl, or ethyl; and
$R_5$ is hydrogen, methyl, ethyl, t-butyl, methoxy, cyanomethyl, or cyanoethyl; and the salts thereof.

3. A compound according to claim 1 wherein Z is oxygen.

4. A compound according to claim 3 wherein $R_4$ and $R_5$ together have at most 4 carbon atoms.

5. A compound according to claim 4 wherein A is haloalkyl of 1 to 4 carbon atoms.

6. A compound according to claim 5 wherein $R_1$ is hydrogen and $R_2$ is hydrogen, halo, methyl, methoxycarbonyl, ethoxycarbonyl, or propoxycarbonyl.

7. A compound according to claim 6, wherein $R_1$ and $R_2$ are hydrogen.

8. A compound according to claim 7, wherein $R_3$ is methoxy, ethoxy, difluoromethoxy, 2,2,2-trifluoroethoxy, methyl, ethyl, fluoromethyl or chloromethy $R_4$ is hydrogen, methyl or ethyl, and $R_5$ is methyl or ethyl.

9. N-(2-Difluoromethoxyphenyl-sulfonyl)-N'-(4-dimethylamino-6-methoxy-1,3,5-triazin-2-yl)-urea according to claim 2.

10. A herbicidal and growth-regulating composition which comprises an effective amount of at least one compound according to claim 1, together with a suitable carrier therefor.

11. A method of controlling undesired plant growth, which method comprises applying thereto or to the locus thereof a herbicidally./effective amount of a compound according to claim 1.

12. A method of regulating plant growth, which method comprises applying thereto or to the locus thereof an effective amount of a compound according to claim 1.

13. A method according to claim 11, for selectively controlling weeds in crops of cultivated plants, which method comprises applying the compound pre-emergence or post-emergence.

14. A method according to claim 13, for controlling weeds in crops of sugar cane, cereals, rice and cotton.

15. A method according to claim 13 for controlling weeds in crops of soybeans.

16. A method according to claim 12 for suppressing plant growth beyond the two-leaf stage, which method comprises applying the compound according to claim 1 pre-emergence.

17. A method of regulating plant growth in order to achieve greater yields, which method comprises applying thereto or to the locus thereof an effective amount of a compound according to claim 1.

18. A method according to claim 17 for regulating plant growth in crops of soybeans.

19. A method according to claim 12 for suppressing the growth of cover crop Leguminosae.

* * * * *